(12) United States Patent
Tadepalli et al.

(10) Patent No.: US 10,202,501 B2
(45) Date of Patent: Feb. 12, 2019

(54) FIBERS TREATED WITH POLYMERIZATION COMPOUNDS AND FIBER REINFORCED COMPOSITES MADE THEREFROM

(71) Applicant: JOHNS MANVILLE, Denver, CO (US)

(72) Inventors: Rajappa Tadepalli, Chennai (IN); Jawed Asrar, Englewood, CO (US); Klaus Friedrich Gleich, Nuremberg (DE); Kiarash Alavi, Littleton, CO (US)

(73) Assignee: Johns Manville, Denver, CO (US)

( * ) Notice: Subject to any disclaimer, the term of this patent is extended or adjusted under 35 U.S.C. 154(b) by 26 days.

(21) Appl. No.: 15/231,580

(22) Filed: Aug. 8, 2016

(65) Prior Publication Data

US 2016/0340494 A1 Nov. 24, 2016

Related U.S. Application Data

(63) Continuation of application No. 12/913,326, filed on Oct. 27, 2010, which is a continuation-in-part of application No. 12/881,736, filed on Sep. 14, 2010, now Pat. No. 8,852,732, which is a continuation-in-part of application No. 12/724,024, filed on Mar. 15, 2010, now Pat. No. 8,378,094, which is a continuation-in-part of application No. 12/008,041, filed on Jan. 8, 2008.

(51) Int. Cl.
| | |
|---|---|
| C03C 13/00 | (2006.01) |
| C08K 7/14 | (2006.01) |
| C07F 7/18 | (2006.01) |
| C08J 5/24 | (2006.01) |
| F03D 1/06 | (2006.01) |
| B29L 31/08 | (2006.01) |

(52) U.S. Cl.
CPC .............. *C08K 7/14* (2013.01); *C03C 13/00* (2013.01); *C07F 7/1836* (2013.01); *C08J 5/24* (2013.01); *F03D 1/0675* (2013.01); *B29L 2031/085* (2013.01); *C08J 2300/22* (2013.01); *C08J 2377/02* (2013.01); *Y02E 10/721* (2013.01); *Y02P 70/523* (2015.11); *Y10T 428/249948* (2015.04)

(58) Field of Classification Search
CPC .......... C08J 5/24; C08J 2377/02; C08J 5/043; Y10T 428/249933; C03C 13/00
See application file for complete search history.

(56) References Cited

U.S. PATENT DOCUMENTS

| | | | |
|---|---|---|---|
| 3,621,001 A | 11/1971 | Steinhofer et al. | |
| 3,833,534 A | 9/1974 | Tierney et al. | |
| 4,105,644 A | 8/1978 | Bukac et al. | |
| 4,188,478 A | 2/1980 | Goebel, Jr. | |
| 4,582,879 A * | 4/1986 | Frisch | C08G 18/00 264/240 |
| 4,697,009 A | 9/1987 | Deschler et al. | |
| 5,240,974 A | 8/1993 | Lechner et al. | |
| 5,782,908 A | 7/1998 | Calahan et al. | |
| 5,864,007 A | 1/1999 | Schmid et al. | |
| 3,013,855 A | 1/2000 | McPherson et al. | |
| 6,358,557 B1 | 3/2002 | Wang et al. | |
| 6,579,965 B2 | 6/2003 | Hoogen et al. | |
| 8,293,322 B2 * | 10/2012 | Burghardt | B29C 47/0004 427/214 |
| 9,452,569 B2 * | 9/2016 | Tadepalli | B29C 70/36 |
| 2003/0096904 A1 | 5/2003 | Hakula et al. | |
| 2007/0072199 A1 | 3/2007 | Levicky et al. | |
| 2010/0286343 A1 | 11/2010 | Burghardt | |

FOREIGN PATENT DOCUMENTS

| | | |
|---|---|---|
| JP | 04122774 | 4/1992 |
| JP | 08 291186 | 11/1996 |
| WO | 2003084583 | 10/2003 |

* cited by examiner

*Primary Examiner* — Gregory Listvoyb
(74) *Attorney, Agent, or Firm* — Robert D. Touslee

(57) ABSTRACT

Methods of making fiber reinforced composite articles are described. The methods may include treating fibers with a sizing composition that includes a polymerization compound, and introducing the treated fibers to a pre-polymerized composition. The combination of the treated fibers and pre-polymerized composition may then undergo a temperature adjustment to a polymerization temperature at which the pre-polymerized composition polymerizes into a plastic around the fibers to form the fiber-reinforced composite article. Techniques for introducing the treated fibers to the pre-polymerized composition may include pultrusion, filament winding, reactive injection molding (RIM), structural reactive injection molding (SRIM), resin transfer molding (RTM), vacuum-assisted resin transfer molding (VARTM), long fiber injection (LFI), sheet molding compound (SMC) molding, bulk molding compound (BMC) molding, a spray-up application, and/or a hand lay-up application, among other techniques.

10 Claims, 5 Drawing Sheets

FIBERS TREATED WITH POLYMERIZATION COMPOUNDS AND FIBER REINFORCED COMPOSITES MADE THEREFROM

CROSS-REFERENCES TO RELATED APPLICATIONS

This application is a continuation of U.S. application Ser. No. 12/913,326 filed Oct. 27, 2010, which is a continuation-in-part of prior U.S. application Ser. No. 12/881,736 filed Sep. 14, 2010, now U.S. Pat. No. 8,852,732 issued Oct. 7, 2014, which is a continuation-in-part of prior U.S. application Ser. No. 12/724,024 filed Mar. 15, 2010, now U.S. Pat. No. 8,378,094 issued Feb. 19, 2013, which is a continuation-in-part of U.S. application Ser. No. 12/008,041 filed Jan. 8, 2008, now abandoned. The entire contents of the above-identified applications are herein incorporated by reference for all purposes.

BACKGROUND OF THE INVENTION

Fiber-reinforced composites are used in a variety of parts and equipment, including automotive parts, boat parts, building elements, and aircraft parts, among other types of articles. One well established method of making these articles is to place the bare fibers in a mold and then flow in the liquid precursors of a thermoset polymer. Once the precursors have infused through the fibers and filled the mold, a curing stage ensues where the precursor polymerize into a thermoset polymer matrix surrounding the fibers. The fiber-reinforced composite may then be released from the mold and, if necessary, shaped, sanded, or otherwise processed into the final article.

Producing fiber-reinforced composites with widely available glass fibers and uncured thermoset resins is inexpensive and usually does not require complex equipment or extreme processing conditions (e.g., high temperatures) to produce the final articles. Still, there are significant disadvantages associated with making fiber-reinforced thermoset articles, as well as deficiencies with the composites in many applications. One considerable disadvantage with making these articles is the health and safety problems posed by working with uncured thermoset resins. These resins often produce a lot of volatile organic compounds (VOCs), many of which are irritants and even carcinogens. Outgasing VOCs are particularly problematic during curing processes when exothermic polymerization reactions raise the temperature of the composite and increase rate which these compounds evaporate into the surrounding atmosphere. In order to prevent VOC concentrations from exceeding safe limits, expensive ventilation and air treatment equipment is required. This equipment is particularly costly and difficult to maintain for the manufacture of larger composite articles, such as boat hulls and wind-turbine blades.

Another significant problem with making fiber-reinforced thermoset composites is the large amounts of unrecyclable waste they generate. Glass reinforced polyester and epoxy wastes do not easily decompose, making them expensive to landfill. When they are contaminated with toxic precursors, such as epoxy prepregs, they present an even greater environmental challenge. The inability to recycle most fiber-reinforced thermosets also presents a disposal challenge when the articles made from these composites reach the end of their useful lives. The size of this challenge only increases with the size of the articles that must be discarded.

Larger-sized articles present additional challenges for thermoset composites. Thermosets in general cannot be welded or melted, which makes it very difficult, if not impossible, to modify or repair thermoset parts once they have been cured. The high degree of crystallinity that is characteristic of many thermoset polymers also makes the composites prone to fractures that cannot easily be repaired. When fractures and other defects form in larger thermoset articles, often the only option is to replace the article at significant cost.

In view of the significant difficulties with both the manufacture and properties of larger articles made from fiber-reinforced thermoset composites, alternative materials are being investigated. One area receiving interest in replacing or blending the thermoset polymers with thermoplastic polymers. Thermoplastics have advantages over thermosets in many article applications, including a usually superior fracture toughness and chemical resistance that can increase the damage tolerance and useable lifetimes in larger articles. The increased toughness of fiber-reinforced thermoplastic composites often means less material is needed to make an article.

Starting monomers for many thermoplastics are less toxic than those of widely used thermosets, and they produce significantly less noxious gases during article production. Many thermoplastics are also meltable and weldable, which allows larger parts to be repaired instead of prematurely replaced. Thermoplastics are generally also recyclable, which significantly decreases environmental impact and waste disposal costs both during manufacturing as well as at the end of an article's lifecycle.

Unfortunately, thermoplastics also have production challenges including significantly higher flow viscosities than uncured thermoset resins. The flow viscosities of widely used thermoplastic polymers may be orders of magnitude higher than uncured epoxy, polyester, and vinylester thermoset resins, which have flow viscosities comparable to water. The higher flow viscosities makes it difficult for thermoplastic resins to infiltrate a fiber mat and produce a homogeneous polymer matrix composite that is free of voids and seams. Oftentimes, it is necessary to introduce the thermoplastic resin under high temperature or high vacuum, which increases the costs and complexity of manufacturing processes. Thus, there is a need for new methods and materials to make fiber-reinforced plastic composites with reduced production problems and improved bonding between the fibers and the polymer matrix. These and other issues are addressed in the present application.

BRIEF SUMMARY OF THE INVENTION

Embodiments of the invention include methods of making fiber reinforced composite articles. The methods may include treating fibers with a sizing composition that includes a polymerization compound, and introducing the treated fibers to a pre-polymerized composition. The combination of the treated fibers and pre-polymerized composition may then undergo a temperature adjustment (e.g., heating) to a polymerization temperature at which the pre-polymerized composition polymerizes into a plastic around the fibers to form the fiber-reinforced composite article. Techniques for introducing the treated fibers to the pre-polymerized composition may include pultrusion, filament winding, reactive injection molding (RIM), structural reactive injection molding (SRIM), resin transfer molding (RTM), vacuum-assisted resin transfer molding (VARTM), long fiber injection (LFI), sheet molding compound (SMC)

molding, bulk molding compound (BMC) molding, a spray-up application, and/or a hand lay-up application, among other techniques.

Embodiments of the invention further include additional methods of making a fiber-reinforced composite article. The methods may include providing fibers to an article template, where the fibers have been treated with a sizing composition that includes a polymerization compound, such as an uncoupled initiator compound, a coupling-initiator compound and/or a catalyst, among other compounds. The methods may further include providing a pre-polymerized mixture to the article template, where the pre-polymerized mixture may include a monomer, and optionally a catalyst. The combination of the fibers and the pre-polymerized mixture may be heated to a polymerization temperature where the monomers polymerize around the fibers and form at least a portion of the composite article. The article may then be removed from the article template.

Embodiments of the invention still further include additional methods of making a fiber-reinforced composite article. The methods may include providing a pre-polymerized fiber-containing material comprising fibers in contact with a combination of a monomer, and optionally a polymerization catalyst, where the fibers have been treated with a polymerization compound. The method may also include applying the pre-polymerized fiber-containing material to an article template, and heating the pre-polymerized fiber-containing material to a polymerization temperature. The monomers polymerize around the fibers to form at least a portion of the composite article.

Embodiments of the invention may include one or more treated fibers that promote a polymerization reaction to form a fiber-reinforced composite article. The treated fiber may have at least one treated surface that includes a polymerization compound. The polymerization compound may initiate or catalyze the polymerization of a pre-polymerized composition to form a plastic matrix of the fiber-reinforced composite article.

Embodiments of the invention also include fiber-reinforced composite articles. The articles may include a plastic polymer matrix and fibers coupled to the matrix by a reacted polymerization compound that was provided with the fibers through treatment with a sizing composition prior to the fibers being introduced to the pre-polymerized composition that polymerizes into the plastic polymer matrix. The polymerization compound may initiate the polymerization of a pre-polymerized composition to form the plastic polymer. Examples of the fiber-reinforced composite articles may include wind turbine blades for electric power generation, among other articles.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

Figure 1A:
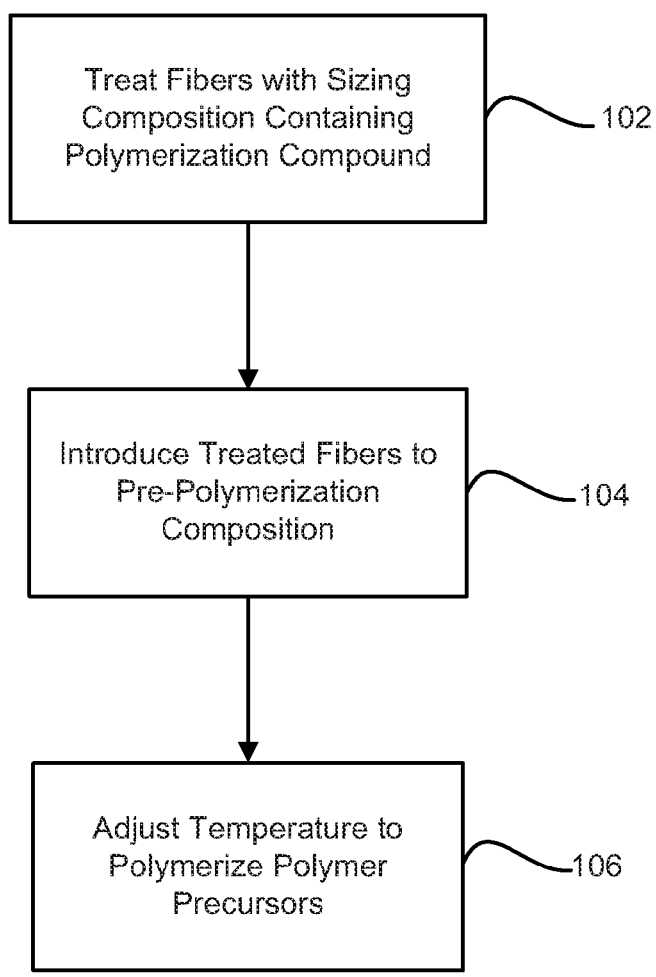
FIG. 1A shows a flowchart with selected steps in methods of making fiber-reinforced composite articles according to embodiments of the invention.

Articles made from fiber-reinforced plastic polymer composites are described, as well as methods of making these articles. These articles include, without limitation, equipment and parts for various transportation vehicles such as cars, trucks, boats, aircraft, trains, and non-motorized vehicles such as bicycles and sailboats, among other kinds of transportation vehicles. The articles may further include equipment and parts used in industrial applications, including parts for electric power generation, such as wind turbine blades.

The present composite materials may be used to make large-sized articles that were previously made from a greater number of smaller pieces which were coupled together to make the larger article. The ability of the composites to make the article from a smaller number of pieces, or even a single piece, reduces manufacturing complexity as well as the number of joints, fasteners, and seams that can weaken the overall structural integrity of the article. An exemplary longest dimension for a large article may be about 1 meter or more, about 5 meters or more, about 10 meters or more, about 15 meters or more, about 20 meters or more, about 25, 30, 35, 40, 45, 50, 55, 60, 65, 70, 75, 80, 85, 90, 95, or 100 meters or more, among other ranges of a longest dimension.

The present methods permit the formation of fiber-reinforced composite articles of larger sizes, increased fracture toughness and corrosion resistance, and longer operational lifetimes. These methods include the use of fibers treated with a sizing composition that contains one or more polymerization compounds that initiate and/or catalyze the polymerization of a pre-polymerized composition to form a polymer matrix of the composite. Polymerization compounds may include catalysts, and uncoupled initiators compounds that are not covalently bonded to a surface of the fiber. They may also include coupling-initiator compounds that have a coupling moiety designed to react with and bond to the fiber, and a more distal positioned initiator moiety that can cause the polymerization of a pre-polymerized composition surrounding the fibers. Exemplary sizing compositions may include combinations of uncoupled polymerization initiators, polymer catalysts, and/or coupling-initiator compounds.

The ratio of uncoupled initiators to coupling-initiator compounds may be adjusted to balance the strength and fracture toughness (i.e., impact resistance) of the final fiber-reinforced composite article. In many instances, strong covalent bonding between the fibers and surrounding plastic matrix created by coupling-initiator compounds enhance the overall strength of the composite article. However, too much of this bonding can reduce the fracture toughness of the article, creating a trade-off between strength and fracture toughness. By introducing a combination of uncoupled initiator compounds and coupling-initiator compounds in the sizing composition, the degree of strong covalent bonding between the fibers and surrounding plastic matrix may be controlled to strike the desired balance between strength and fracture toughness in the composite article.

The plastic matrix of the composite articles may be made from thermosets, thermoplastics, or a combination of both. When the matrix includes one or more thermoplastics, embodiments of the present methods can address problems of high flow viscosity melted thermoplastics that complicate the formation of the final composite article. These embodiments may include forming the polymer matrix in situ in an article mold, instead of forming and melting the polymers before incorporating (e.g., injecting) them into the mold. This allows the lower viscosity monomers to be incorporated into the mold and infused around the fibers at lower temperatures, in shorter times, and with fewer voids and other defects caused by a slow flowing melted polymer.

The combinations of the pre-polymerized composition and polymerization compound may be selected to have a controllable difference between the melting temperature of the pre-polymerized composition and its polymerization temperature. For example, the melting temperature of the composition may be lower by about 10° C. or more than its polymerization temperature. This permits the composition to be melted and incorporated into an article mold for a controlled period of time before increasing the monomer to its polymerization temperature to perform in situ polymerization. It also permits variable control of the timing of the polymerization stage instead of having to work within a fixed, predetermined time of polymerization. For example, inspections and quality checks may be performed to insure the pre-polymerized composition is homogeneously distributed in the mold before the temperature is raised to the polymerization temperature. In contrast, many conventional methods require fixed polymerization times that cannot be significantly accelerated or delayed.

The pre-polymerized composition may be liquid or solid at room temperature. When the pre-polymerized mixture is a solid, it may be introduced to the mold or treated fibers as a solid (e.g., particles, fiber prepreg, etc.) before raising the temperature to between the melting and polymerization temperature. This allows the pre-polymerized composition to melt and infuse around the fibers, and conform to the shape of the mold when a mold is used, before being polymerized. Examples may further include adding combinations solid and liquid pre-polymerized composition to the treated fibers prior to and/or during polymerization.

Exemplary Methods

FIG. 1A shows selected steps in an exemplary method 100 of making a fiber-reinforced composite article according to embodiments of the invention. The method 100 may include the step of treating fibers with a sizing composition that includes at least one polymerization compound 102. The method may further include introducing together a pre-polymerization composition and the treated fibers 104. Techniques for introducing the composition and fibers may include pultrusion, filament winding, reactive injection molding (RIM), structural reactive injection molding (SRIM), resin transfer molding (RTM), vacuum-assisted resin transfer molding (VARTM), long fiber injection (LFI), sheet molding compound (SMC) molding, bulk molding compound (BMC) molding, a spray-up application, and/or a hand lay-up application, among other techniques.

The method 100 may further include the step of adjusting the temperature of the combination of the treated fibers and pre-polymerized composition to a polymerization temperature at which the pre-polymerized composition polymerizes into a plastic matrix around the fibers to help form the fiber-reinforced composite article 106. After the polymerizing combination is held at the polymerization temperature for set period of time, the temperature may be adjusted again to allow the article to cool and set. When the composition is added in the liquid phase, it has a temperature at or above the melting point of the precursors and other components, but below a temperature where significant polymerization occurs.

In addition to the polymerization compound, the sizing composition may further include one or more solvents (e.g., water), film forming agents, lubricants, and/or silanes, among other components. The lubricants help protect the surface of the fibers from scratches and abrasions commonly caused by fiber-to-fiber contact and friction during processing. The silanes may act as chemical linking agents by bonding to both the glass fiber and the plastic matrix. Silanes containing organosilane groups may be coupling agents for glass fibers and organic polymers, and serve to bond the two materials in the composite article. Film formers can provide a desired degree of bonding between the fibers in the fiber strands to avoid fuzzing and excess filamentation during processing in fiber manufacturing operations and/or fiber composite fabrication operations. The sizing composition may be applied to the fibers by spraying and/or mixing, followed by drying to form the treated fibers.

The pre-polymerized composition that forms the plastic matrix may include polymerizable precursors of thermoplastics such as polybutylene terephthlalate (PBT), polyethylene terephthalate (PET), polyamide-6 (PA-6), polyamide-12 (PA-12), polyamide-6,6 (PA-6,6), cyclic poly(1,4-butylene terephthalate) (CBT), polyurethanes (TPU), polymethylmethacrylate (PMMA), polycarbonates (PC), polyphenylenesulphide (PPS), polyethylenenapthalate (PEN), polybutylenenaphthalate (PBN), polyether etherketone (PEEK), and polyetherketoneketone (PEKK), and combinations of two or more of these polymers, among other polymers.

One exemplary pre-polymerized composition includes lactam monomers that produce polyamide (also called nylon) when polymerized. The lactam monomers may have the formula:

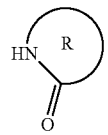

where R represents a $C_3$ to $C_{12}$ substituted or unsubstituted cyclic hydrocarbon chain. The polymerization of these lactam monomers involves the opening of the cyclic hydrocarbon chain to make a linear chain with reactive carbonyl and amine groups separated by a —$(CH_2)_n$— hydrocarbon group.

One exemplary lactam monomer that enjoys wide commercial use is caprolactam, which polymerizes into nylon 6. Other lactam monomers may include butyrolactam (also known as 2-pyrrolidone) which polymerizes into nylon 4;

valerolactam which polymerizes into nylon 5; capryllactam which polymerizes into nylon 8; and lauryllactam which polymerizes into nylon 12; among other lacatams.

Another exemplary pre-polymerized composition includes one or more macrocyclic polyester oligomers, that polymerize form a polyester thermoplastic. Examples of these macrocyclic polyester oligomers include polybutylene terephthalates, such as cyclic poly(1,4-butylene terephthalate).

The polymerization compound, or compounds, may include polymerization catalysts, polymerization activators, uncoupled polymerization initiator compounds, and/or coupling-initiator compounds, among other compounds. The uncoupled polymerization initiator compounds may include an initiator compound having a formula:

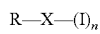

wherein n is an integer with a value of 1 to 5;

R comprises a terminal moiety selected from the group consisting of a hydrogen and a hydrocarbyl group;

X comprises a linking moiety that links the R moiety with the one or more I moieties; and $(I)_n$ comprises one or more polymerization initiator moieties, wherein each of the initiator moieties is capable of initiating a polymerization of the pre-polymerized composition, and wherein each of the initiator moieties is the same or different.

Examples of the terminal moiety (R) may include a hydrogen atom, a hydrocarbon moiety such as $CH_3$—, $C_nH_{2n+1}$— where n is an integer from 2 to 20, an aromatic group such as a phenyl group, or an amine group, among other terminal moieties.

Examples of the linking moiety (X) may include a covalent bond, an alkyl group, an aryl group, an alkene group, or an amine group, among other linking moieties.

When the pre-polymerized composition is a lactam precursor of a polyamide, the polymerization initiator moieties may have the formula:

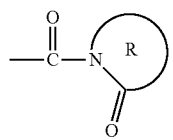

where the carbonyl group is bonded to a linking moiety of the initiator compound and R represents a $C_3$ to $C_{12}$ substituted or unsubstituted cyclic hydrocarbon chain. When the combination of the pre-polymer lactam mixture and fibers is raised to the polymerization temperature, the ring structure may open or be otherwise activated to initiate a branched or unbranched polymerized chain from the initiator moiety. For example, the initiator moiety may have the formula:

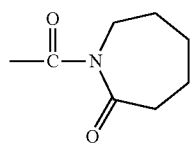

In additional examples, the initiator compound may be formed from two or more initiator precursors that react in situ to form the initiator compound. For example, one of the initiator precursors may be a polymerization compound in the sizing composition, while a second initiator precursor may be included in the pre-polymerized composition that is introduced to the treated fibers having the first initiator compound. When the treated fibers and pre-polymerized composition are introduced, the first and second initiator precursors may react to form the initiator compound capable of initiating the polymerization of the polymerizable precursors in the pre-polymerized composition into the plastic around the fibers.

A specific example of a multi-part initiator system includes ethyl benzoate acting as a first initiator precursor polymerization compound in the sizing composition used to treat the fibers, and sodium caprolactam acting as a second initiator precursor included in the pre-polymerized composition with lactam polymerizable precursors and a catalyst. When the treated fibers are introduced to the pre-polymerized composition, the ethyl benzoate reacts with the sodium caprolactam around the fibers to form the initiator.

Exemplary polymerization compounds may include catalysts. For example, when the pre-polymerized composition includes polymerizable lactam compounds, the catalysts may include cationic catalysts, anionic catalysts, and/or water. In cationic polymerizations, the catalyst may be an acid that protonates the carbonyl oxygen and/or nitrogen group on the lactam to start a nuclephilic reaction between the protonated monomer and a second lactam monomer. This reaction may be followed by a series of ring-opening acylations of the primary amine to build the polyamide chain.

In anionic polymerizations, the catalyst may include a base such as an alkali metal, alkali-earth metal hydroxide, or alkali metal amide (among other bases) that deprotonates the lactam nitrogen to form an anion that reacts with a second lactam monomer. Subsequent proton transfer and propagation reactions build the polyamide chain. In some instances, the reaction between the initial anion and the second lactam monomer may be further facilitated by an activator compound, such as an acyl halide or anhydride (among other activators).

In hydrolytic polymerizations that involve water, polymerization may be initiated when the water initiates a hydrolysis reaction that opens the lactam ring to form an amino acid. The amine group of the amino acid then reacts with additional lactam monomers in subsequent ring-opening reactions to build the polyamide chain.

When the pre-polymerized compound includes macrocyclic polyester oligomers, exemplary catalysts may include tin-containing compounds and/or titanium-containing compounds. For example the catalysts may include organotin and/or organotitanate compounds. Tin-containing compounds may include monoalkyltin(IV) hydroxide oxides, monoalkyltin(IV) chloride dihydroxides, dialkyltin(IV) oxides, bistrialkyltin(IV) oxides, monoalkyltin(V) trisalkoxides, dialkyltin(IV) dialkoxides, and trialkyltin(IV) alkoxides, among other tin-containing compounds. Exemplary titanium-containing compounds include titanate tetraalkoxide compounds (e.g., tetraisopropyl titanate) and tetraalkyl titanate compounds (e.g., tetra(2-ethylhexyl) titanate), among others.

Exemplary polymerization compounds may include coupling-initiator compounds. Specific coupling-initiator compounds may be selected based on the type of fiber and plastic used in the composite. Generally speaking, the coupling-initiator compounds may have the formula $C—X—(I)_n$, where C represents the coupling moiety, $(I)_n$ represents n polymerization initiator moieties, and X represents a linking moiety that links the C moiety to the one or more I moieties.

When the fibers are glass fibers, the coupling moiety C may include one or more silicon groups, and the coupling-initiator compound may be represented by the formula S—X—(I)$_n$, where S represents a silicon-containing coupling moiety and X and (I)$_n$ have the same meaning as described above.

The fibers may be made from a material that can be treated with the sizing composition that includes the polymerization compound. Examples of fibers include glass fibers (e.g., E-glass, etc.), ceramic fibers (e.g., aluminum oxide, silicon carbide, silicon nitride, silicon carbide, basalt, etc.), carbon fibers (e.g., graphite, semi-crystalline carbon, carbon nanotubes, etc.), metal fibers (e.g., aluminum, steel, tungsten, etc.), and polymer fibers (e.g., aramid, etc.). The fibers may be arranged as a mono-axial and/or multi-axial, woven and/or non-woven mat. In addition, the fibers may also include chopped and/or unchopped (i.e., continuous fibers). The mats may have multiple sections with different weave styles, as well as combinations of woven and non-woven sections. In addition, the mats may have regions where chopped fibers are incorporated, for example to allow better wet out and resin penetration in a preselected part or parts of the composite article.

Figure 1B:
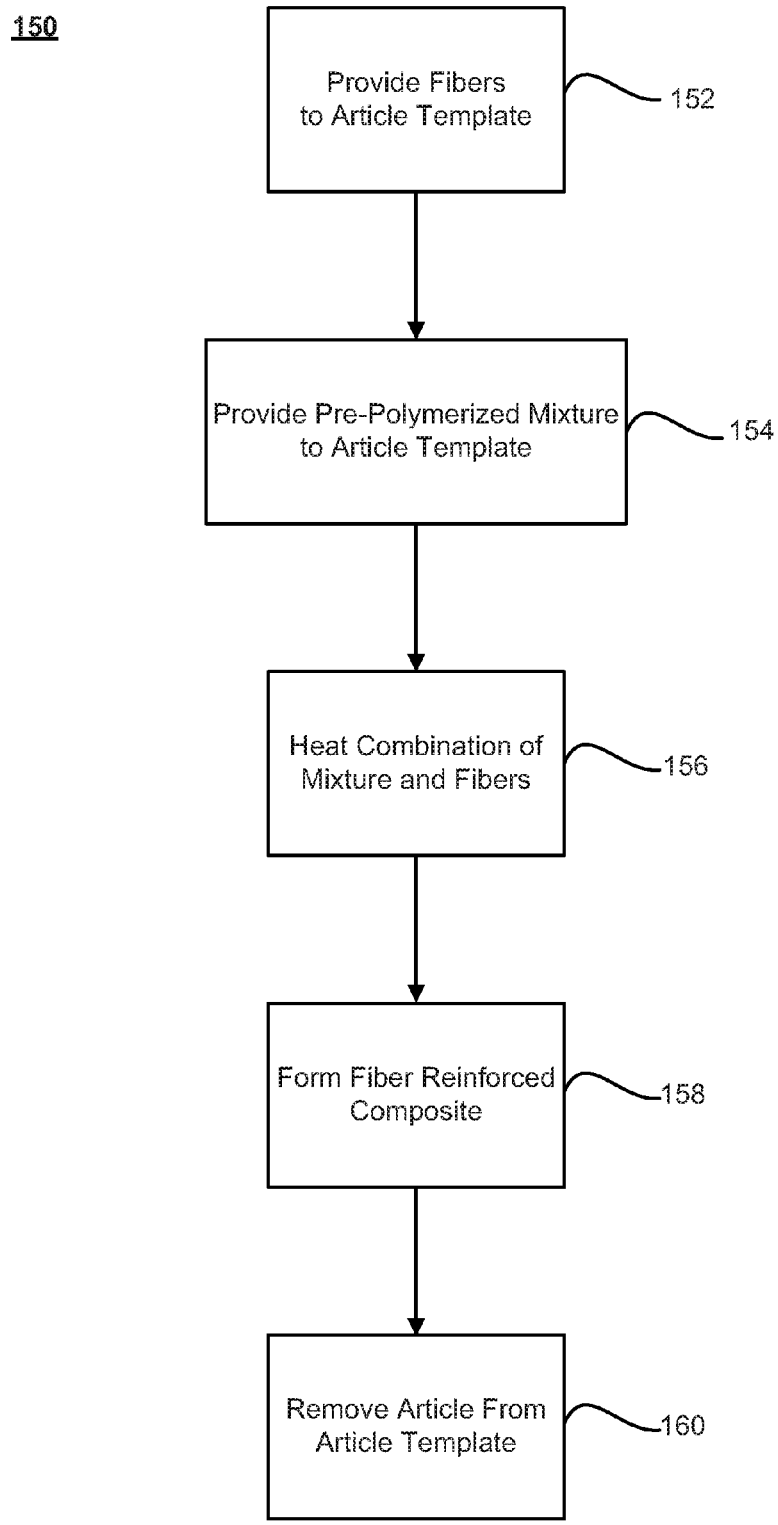
FIG. 1B shows a flowchart with selected steps in additional methods of making fiber-reinforced composite articles according to embodiments of the invention.

FIG. 1B shows selected steps in an exemplary method 150 of making a fiber-reinforced composite article according to embodiments of the invention. The method 150 may include the step of providing fibers to an article template 152. The fibers are treated with a sizing composition that includes one or more polymerization compounds that facilitate the polymerization of a pre-polymerized composition that forms a plastic matrix in the composite article. These polymerization compounds may include, a catalyst, an activator, a polymerization initiator, and/or a coupling-initiator compound.

The method 150 may further comprise providing a pre-polymerized composition to the article template 154. The pre-polymerized composition may include precursor monomers and/or oligomers of the plastic, polymerization catalysts, and/or polymerization initiators, among other components. The pre-polymerized composition may include partially polymerized compounds such as dimers, trimers, and/or oligomers of the plastic. The pre-polymerized composition may be added in the liquid phase to the article template, or added in the solid phase. When the composition is added in the liquid phase, it has a temperature at or above the melting point of the precursors and other components, but below a temperature where significant polymerization occurs. When the composition is added in the solid phase, it may be added as particles to the article template and/or exist as a pre-impregnated ("pre-preg") coating on the fibers that are added to the template. Embodiments further include providing the pre-polymerized composition as both a liquid-phase mixture and solid-phase mixture to the article template.

In liquid-phase additions, the polymer precursors and the catalyst/initiator components may be kept separate until they are provided to the article template. For example, a catalyst may be combined with the liquid-phase monomer immediately before or during there introduction (e.g., injection) into the article template. Alternatively, a monomer and catalyst may be combined and stored as a solid or liquid pre-polymerized mixture well before their introduction to the article template. While the liquid and solid phase mixtures of the pre-polymerized composition may exhibit some degree of polymerization—for example the formation of dimers, trimers, and/or other oligomers—they are still considered pre-polymerized since substantially complete polymerization has not occurred. Similarly, pre-preg fibers that have a coating of B-stage thermoplastic materials surrounding the fibers may still be considered a pre-polymerized mixture or a component of the pre-polymerized mixture. For purposes of this application, discussions of the polymerization of pre-polymerized compositions include polymerizations of dimers, trimers, and/or other oligomers, as well as monomers of the polymer.

After the pre-polymerized composition is provided to the article template and has made sufficient contact with the fibers, the combination of composition and fibers may be heated to a temperature where significant polymerization occurs, as shown in step 156. For example where the pre-polymerized composition includes caprolactam, the temperature of the pre-polymerized mixture may be raised from a melting temperature of between about 80° C. and 120° C., to a polymerization temperature of about 120° C. or more (e.g., about 120° C. to about 220° C.). In additional examples, the pre-polymerized composition may have a melting temperature of about 80° C. to about 200° C. (e.g., about 100° C. to about 160° C.), and may have a polymerization temperature of about 120° C. to about 220° C. (e.g., about 180° C. to about 220° C.).

At the polymerization temperature, the polymerization-initiator moieties facilitate polymerization around the fibers. As described above, in the case of caprolactam the initiator moieties may have the formula:

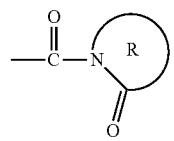

where the carbonyl group is bonded to a linking moiety of the coupling-initiator compound and R represents a $C_3$ to $C_{12}$ substituted or unsubstituted cyclic hydrocarbon chain. When the combination of the caprolactam-containing, pre-polymerized composition and treated fibers is raised to the polymerization temperature, the ring structure may open or be otherwise activated to initiate a branched or unbranched polymerized chain from the initiator moiety.

At least a portion of the plastic matrix is formed by the polymerization of the caprolactam monomers around the treated fibers. The initiator moieties may start the formation of straight and/or branched polyamide polymers whose formation is also aided by the one or more catalysts supplied by the treated fibers, the pre-polymerized composition, or both. When coupling-initiator compounds are included in the treated fibers, they create a covalently-bonded link between the surface of the fibers and the surrounding polymers that is significantly stronger than a bond formed by simply curing a polyamide resin in the presence of untreated fibers.

The plastic matrices may also include polymers that are not directly bonded to the treated fibers. These polymers may have been formed, for example, through polymerizations that were not initiated at an initiator moiety, and polymers that have fragmented or decoupled after polymerization was initiated at the moiety. Although these polymers may not be directly bonded to the fibers, their columbic and physical interactions with the directly bonded polymers may further strengthen the bonding between the treated fibers and the surrounding polymer matrix.

As the polymerization of the polymer precursors around the fibers progress, a fiber-reinforced composite is formed in the article template. The composite material may form a portion or whole of the composite article 158. The shape of the composite article may be defined, at least in part, by the shape of the article template, which acts as a mold. For example, the article template may be shaped such that the composite forms the front or back halves of a wind turbine blade that are joined in subsequent production steps. Alternatively, the article template may be designed for a one-shot fabrication of the composite article (e.g., forming both halves of the blade from a single article template).

When the composite material has had sufficient time to solidify, it may be removed from the article template 160. In some instances, removal may be facilitated by applying release agents to the surfaces of the article template that are exposed to the fibers and pre-polymerized composition that form the composite article. These release agents hinder the fibers and polymerizing precursors from binding with the template as the composite is formed.

The composite material may be removed from the template either before or after the plastic matrix has fully formed. In instances where the composite material is removed before curing is completed, the curing has progressed to the point where the article is sufficiently solid to retain the shape of the article after removal from the template. The removed article may undergo subsequent processing steps, such as sanding, cutting, polishing, washing, drilling, coating, and/or painting, among other post-formation steps. In the case where the composite is a portion of an article, the removed article may undergo steps to form the whole article, such as gluing, gap filling, and/or fastening the composite to other components to make the whole article.

Figure 2:
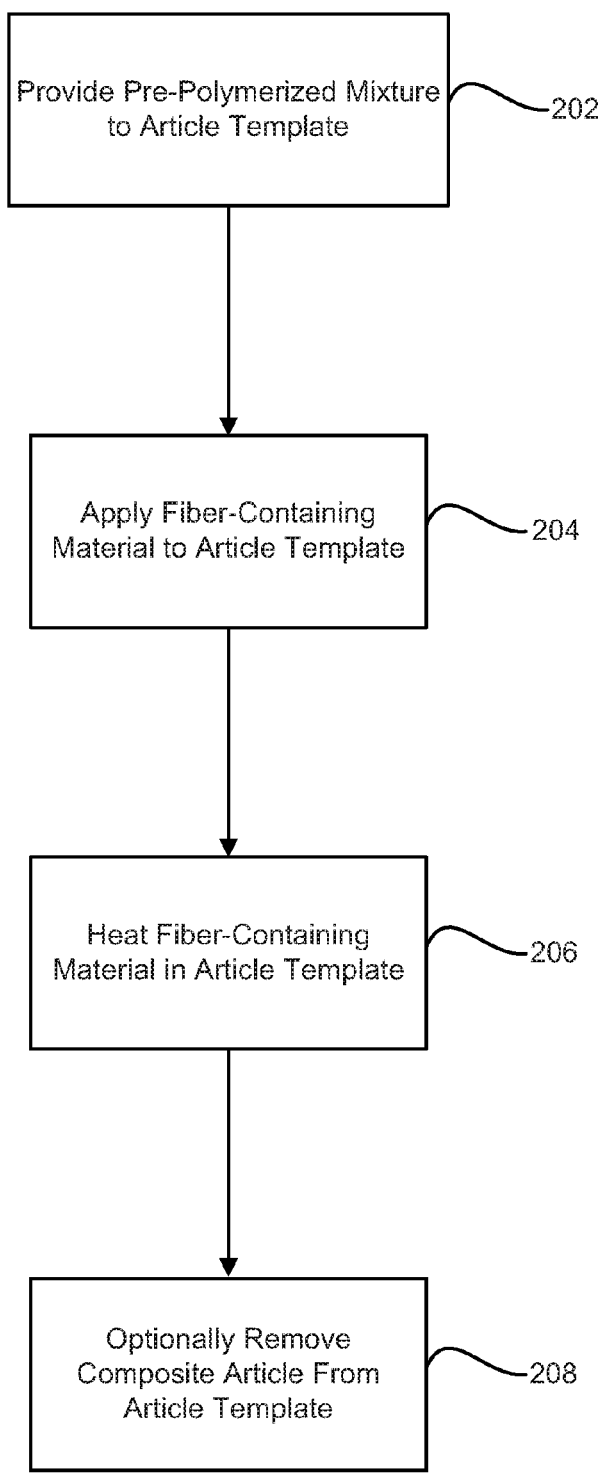
FIG. 2 shows a flowchart with selected steps in additional methods of making fiber-reinforced composite articles according to embodiments of the invention.

Referring now to FIG. 2, a flowchart outlines selected steps in additional methods of making fiber-reinforced composites according to embodiments of the invention. The methods 200 may include providing a pre-polymerized fiber containing material (e.g., a pre-preg), where the fibers are in contact with a combination of the polymer precursors (e.g., monomers, oligomers) and a polymerization catalyst 202. Examples of the pre-polymerized fiber may include glass fibers that have been pre-treated with a sizing composition that includes at least one polymerization compound and coated with a pre-polymerized composition that includes polymer precursors, and optionally polymerization catalyst. The pre-polymerized composition may be applied above a melting temperature for the polymer precursors, but below a temperature where significant polymerization occurs. Following the application of the pre-polymerized composition, the treated fibers may be cooled to solidify the coating and stored until use.

That use may include applying the pre-polymerized fiber-containing material to an article template 204 that may act as a mold for a composite article. The pre-polymerized fiber-containing material may be applied as a lay-up of fiber materials in the article template. In some embodiments the fibers may be arranged in a fiber mat before being applied to the template, or arranged to have a particular orientation or set of orientations during and/or after being layed-up in the template.

The methods 200 may optionally include applying additional layers of fiber-containing material to the article template. These additional layers may consist of untreated fibers, fibers treated with additional polymerization compounds, and additional layers of pre-polymerized fiber-containing material. The fiber layers may be stacked on top of each other, and/or may be applied side-by-side in the article template. Embodiments may include positioning the pre-polymerized fiber-containing material in specific locations of the article template to enhance the strength and mass of the composite material in those areas. For example, one or more layers (or sections of layers) of the pre-polymerized fiber-containing material may be positioned where the outer shell (i.e., skin) of wind turbine blade makes contact with an internal support structure of the blade such as a rib and/or spar.

The methods 200 may also optionally include providing the same or different pre-polymerized composition to the article template following the lay-up of the fiber-containing materials. The pre-polymerized composition may include the same or different make up of polymer precursors and/or catalysts, and may be provided to the fiber materials in the article template by, for example, resin transfer molding (RTM), vacuum-assisted resin transfer molding (VARTM), among other techniques.

After the pre-polymerized fiber-containing material (and any additional materials) have been applied to the article template, the materials may be heated to a temperature where the pre-polymerized composition polymerizes to form a composite material 206. The polymerization processes may include the activation of an initiator moiety on initiator and/or coupling-initiator compounds present in the treated fiber. These moieties start the formation of polymers (e.g., polyamide polymers) that surround the fibers of fiber composite. This composite may form either a portion or whole of a fiber-reinforced composite article.

In some embodiments, the article template (or a portion thereof) may become part of the composite article. In these embodiments, the fiber-reinforced composite is bonded to one or more surfaces of the article template that were exposed to the pre-polymerized fiber-containing material. The composite article that is formed includes an outer layer made from the article template. In additional embodiments, the fiber-reinforced composite may optionally be removed from the article template 208, and the template may be discarded or prepared for forming another composite article.

Exemplary Methods of Making a Wind Turbine Blade

Figure 3:
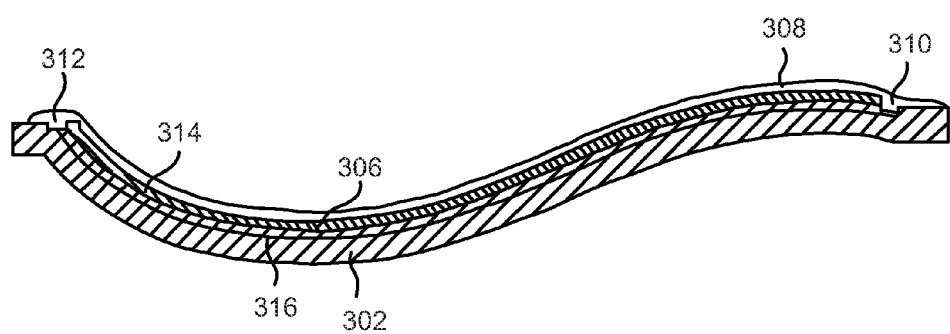
FIG. 3 illustrates a simplified cross-sectional drawing of an article template for making a wind turbine blade according to embodiments of the invention.
Figure 4:
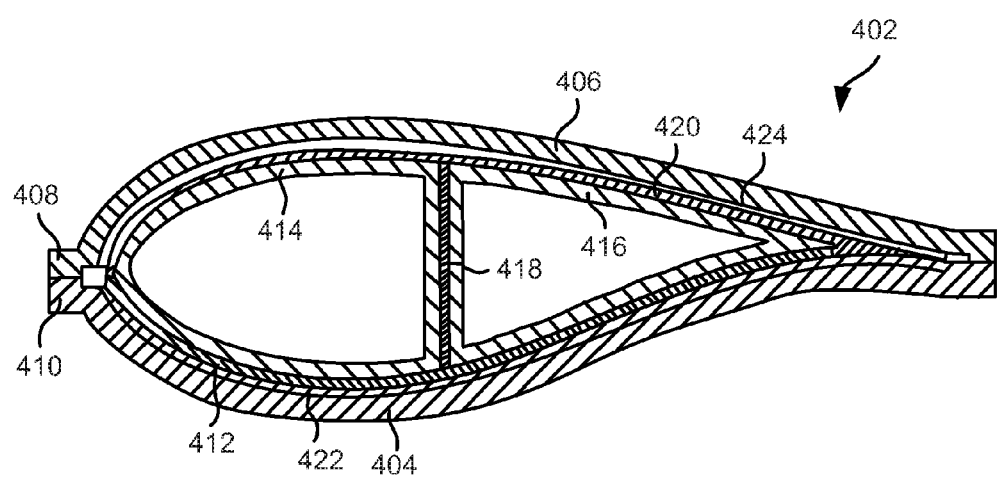
FIG. 4 illustrates a simplified cross-sectional drawing of an article template for a one-shot method of making a wind turbine blade according to embodiments of the invention.

Exemplary methods of making a wind turbine blade will now be described with reference to the article templates shown in FIGS. 3 and 4 respectively. FIG. 3 shows an article template 302 for part of the outer skin of a wind turbine blade made from a fiber reinforced composite. The template 302 may be for the side of the blade which faces the wind during operation of the turbine. A second article template (not shown) is used to form the opposite side of the blade. The two skins may then be joined using fasteners, adhesives, gap fillers, etc. to form the outer surface of the blade. Internal blade components, such as spars and ribs, may also be added when the skins are joined together.

The article template 302 may be made from a rigid material that has an inner surface 306 defining the shape of the outer skin. This surface may be made from a material or treated (e.g., coated) to form a exposed layer of material that facilitates the release of the fiber-reinforced composite outer skin from the article template 302.

The article template 302 may further comprise a vacuum bag 308 that may be fluid-tightly sealed to the peripheral edges of the template. Together, the liner of the vacuum bag 308 and inner surface 306 define an enclosed volume where the materials for the composite may be combined and heated to form the fiber-reinforced composite outer skin.

The article template 302 may further include openings 310 and 312, through which pre-polymerized compositions may flow to make contact with the fiber materials shown in fiber layer 314. As noted above, additional pre-polymerized materials (e.g., solid pre-preg materials) may also be present with the fibers in the fiber layer 314.

When the vacuum bag 308 is evacuated, the change in air pressure between the inside and outside of the vacuum bag 308 may press the bag liner against the fiber layer 314. In addition, a pressure differential causes the pre-polymerized composition to flow through openings 310 and 312 to infiltrate the fiber layer 314. In the embodiment shown, the flowing composition may form two fluid fronts at the forward and rear ends of the outer skin which may converge proximate to the middle of the skin. Additional flow configurations are possible depending upon the number and positioning of the openings in the article template.

When the pre-polymerized composition has been distributed over the fiber layer 314, the materials may be heated to a polymerization temperature to start the formation of the fiber-reinforced composite. The heating may, for example, be carried out by a heating element 316 positioned proximate to the inner surface 306 of the article template 302. When the polymerization process is sufficiently advanced, the nascent composite may be allowed to cool at a pre-defined rate to ensure the outer skin is formed with the requisite mechanical properties. The outer skin may then be removed from the article template 302 so that it can be combined with the other parts of the blade. The article template may be treated (e.g., cleaned and prepared) to form another outer skin.

The article template 302 shown in FIG. 3 forms only a part of the outer skin of a wind turbine blade. FIG. 4 shows an article template 402 that is designed to form a more complete outer skin for a wind turbine blade with a one-shot manufacturing technique. The article template 402 includes a first mold component 404 and a second mold component 406 which are combined to form the one-shot article template 402. The first and second mold components may have peripheral edges 408, 410 that can be joined to form an air-tight seal.

One-shot methods of making a wind turbine blade with article template 402 may include laying-up fiber materials in the first mold component 404 to form a first fiber layer 412 in the component. Additional materials such as particles of polymer precursors, initiators, and/or catalysts, may also be added to the mold component 404 and/or fiber layer 412. First and second internal support sections 414, 416 may be placed in the first mold component 404 over the first fiber layer 412. The first and second internal support sections 414, 416 may be made from rigid materials such as wood, ceramic, light-weight metal or alloy, and/or polymers, among other materials. The rigid material may be surrounded by a more flexible material (e.g., foam rubber) and a flexible membrane that may make contact with the fiber layers in the template 402.

An additional fiber layer 418 may support a gap between the first and second support sections 414, 416. This fiber layer 418 may be converted into an internal support of the final composite that joins opposite sides of the blade for increased strength and stability. In additional embodiments, two or more internal supports (or conversely no supports) may be formed in blade.

Another additional fiber layer 420 may be layed-up over the first and second support structures 414, 416 such that the ends of the fiber layer 420 overlap or otherwise contact the complementary ends of first fiber layer 412. The second mold component 406 may then be placed over the fiber layers and internal supports and secured to first mold component 404 along the peripheral edges 408, 410.

Openings (not shown) in the article template 402 may be coupled to vacuum lines that create vacuum channels in the enclosed spaces between the mold components 404, 406, and outer surfaces of support sections 414, 416. When the channels are evacuated, positive pressure exerted from inside the support sections 414, 416 may push their outer flexible membranes into the surrounding fiber layers 412, 420 to press them against inside surfaces of the article template 402. The evacuation of the channels also creates a pressure gradient for the flow of a pre-polymerized composition through the fiber layers.

Following the addition of the pre-polymerized composition with the fiber layers, the combination may be heat cured to polymerize the polymer precursors and form the fiber reinforced composite article. The heating may be done by a heat transfer system 422, 424, such as heating filaments integrated into the first and second mold components 404, 406.

Once the composite article has sufficiently cured, the mold components 404, 406 may be separated and the fiber-reinforced composite wind turbine blade removed from the article template 402.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the fiber" includes reference to one or more fibers and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:
1. A fiber-reinforced composite article comprising:
a polymer matrix; and
treated fibers reinforcing the polymer matrix, wherein the treated fibers include a first initiator precursor comprising ethyl benzoate in contact with a surface on the treated fibers and a second initiator precursor present in a pre-polymerized composition that formed the polymer matrix, wherein the first initiator precursor reacts with the second initiator precursor to form an initiator capable of initiating a polymerization of the pre-polymerized composition to form the polymer matrix.

2. The fiber-reinforced composite article of claim 1, wherein all of the first initiator precursor contacts the fiber surface.

3. The fiber-reinforced composite article of claim 1, wherein all of the first initiator precursor on the fiber surface is exposed to the pre-polymerized composition.

4. The fiber-reinforced composite article of claim 1, wherein the pre-polymerized composition comprises caprolactam.

5. The fiber-reinforced composite article of claim 1, wherein the second initiator precursor comprises sodium caprolactam.

6. The fiber-reinforced composite article of claim 1, wherein the treated fibers also included a coupling-initiator compound covalently bonded to the surface on the treated fibers.

7. The fiber-reinforced composite article of claim 1, wherein the treated fibers also included a polymerization compound in contact with the surface on the treated fibers, wherein the polymerization compound has the formula:

$$R-X-(I)_n$$

wherein n is an integer with a value of 1 to 5;

R comprises a terminal moiety selected from the group consisting of a hydrogen and a hydrocarbyl group, X comprises a linking moiety that links the R moiety with one or more I moieties; and $(I)_n$ comprises one or more polymerization initiator moieties, wherein each of the initiator moieties is the same or different.

8. The fiber-reinforced composite article of claim 7, wherein the polymerization compound non-covalently contacts the surface on the treated fibers.

9. The fiber-reinforced composite article of claim 1, wherein the treated fibers also included a catalyst in contact with the surface on the treated fibers.

10. The fiber-reinforced composite article of claim 9, wherein the catalyst comprises an alkali metal hydroxide or an alkali earth metal hydroxide.

* * * * *